(12) United States Patent
Liao et al.

(10) Patent No.: US 6,610,749 B2
(45) Date of Patent: Aug. 26, 2003

(54) POLYHYDROXYLATED BENZENE-CONTAINING COMPOUNDS

(75) Inventors: Shutsung Liao, Chicago, IL (US); Richard A. Hiipakka, Chicago, IL (US); Yung-Hsi Kao, Chung-Li (TW)

(73) Assignee: ARCH Development Corporation, Chicago, IL (US)

( * ) Notice: Subject to any disclaimer, the term of this patent is extended or adjusted under 35 U.S.C. 154(b) by 0 days.

(21) Appl. No.: 09/783,901

(22) Filed: Feb. 15, 2001

(65) Prior Publication Data

US 2003/0139477 A1 Jul. 24, 2003

Related U.S. Application Data

(60) Provisional application No. 60/183,668, filed on Feb. 18, 2000.

(51) Int. Cl.[7] .............................................. A61K 31/05
(52) U.S. Cl. ...................................... 514/733; 514/734
(58) Field of Search .................................. 514/733, 734

(56) References Cited

U.S. PATENT DOCUMENTS 5,605,929 A   2/1997   Liao et al. .................. 514/456

FOREIGN PATENT DOCUMENTS

| EP | 0 522 502 A1 | 1/1993 |
|---|---|---|
| JP | 5-17352 | 1/1993 |
| WO | WO 99/22728 | 5/1999 |
| WO | WO 00/41708 | 7/2000 |

OTHER PUBLICATIONS

Kao et al., "Modulation of Endocrine Systems and Food Intake by Green Tea Epigallocatechin Gallate", Database CAPLUS on STN., Ben May Institute for Cancer Research (Chicago, IL., USA), CAPLUS No. 2000:257827, abstract, Endocrinology, 2000.

Dulloo et al., "Green Tea and Thermogenesis: Interactions Between Catechin–polyphenols, Caffeine and Sympathetic Activity", Database Embase on STN, Institute of Physiology, University of Fribourg (Fribourg, Switzerland) Embase No. 2000072479, abstract, International Journal of Obesity (US), 2000.

Wang et al., "Interaction of Epicatechins Derived from Green Tea With Rat Hepatic Cytochrome P–450", Drug Metabolism and Disposition 16:98–103, 1988.

*Primary Examiner*—Phyllis G. Spivack
(74) *Attorney, Agent, or Firm*—Fish & Richardson P.C.

(57) ABSTRACT

A method for reducing food intake in a subject and a method for reducing the levels of an endocrine in a subject comprising administering to the subject in need thereof an effective amount of a compound of the formula:

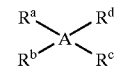

wherein
A is alkenyl, and
each of $R^a$, $R^b$, $R^c$ and $R^d$ is herein defined.

2 Claims, No Drawings

POLYHYDROXYLATED BENZENE-CONTAINING COMPOUNDS

CROSS REFERENCE TO RELATED APPLICATIONS

Pursuant to 35 USC §119(e), this application claims the befit of prior U.S. provisional application No. 60/183,668, filed Feb. 18, 2000.

STATEMENT AS TO FEDERALLY SPONSORED RESEARCH

This invention was made in part with support from the National Institutes of Health (Grants DK41070 and CA 58073). Accordingly, the U.S. government may have certain rights in this invention.

BACKGROUND OF THE INVENTION

In oriental culture, it has been widely believed for a long time that tea has medicinal efficacy in preventing and treatment of many diseases. Scientific and medical evaluation of tea, however, started only very recently. Early epidemiological studies yielded inconclusive evidence whether tea is medically beneficial. It is found that green tea contains polyhydroxylated benzene-containing compounds. Thus, it should be explored whether these compounds or derivatives thereof are beneficial to health.

SUMMARY OF THE INVENTION

An aspect of this invention relates to a method for reducing food intake in a subject. The method comprises administering to the subject in need thereof an effective amount of a compound of formula (I):

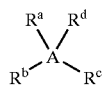
(I)

A is a $C_{1-14}$ hydrocarbon, an oxygen, a sulfur, or a nitrogen. The hydrocarbon is selected from a group consisting of alkyl, alkenyl, alkynyl, cycloalkyl, heterocycloalkyl, cycloalkenyl, heterocycloalkenyl, aryl, and heteroaryl. Each of the just-mentioned moieties is optionally substituted with alkoxy, hydroxyl, hydroxylalkyl, carboxyl, halo, haloalkyl, amino, thio, nitro, cyano, oxo, alkylcarbonyloxy, alkyloxycarbonyl, arylcarbonyloxy, aryloxycarbonyl, alkylcarbonyl, arylcarbonyl, formyl, aminocarbonyl, alkylcarbonylamino, arylaminocarbonyl, or arylcarbonylamino. Each of $R^a$, $R^b$, $R^c$ and $R^d$, independently, is hydrogen, alkyl, alkenyl, alkynyl, cycloalkyl, heterocycloalkyl, cycloalkenyl, heterocycloalkenyl, aryl, heteroaryl, aralkyl, heteroaralkyl, alkoxy, hydroxyl, hydroxylalkyl, carboxyl, halo, haloalkyl, amino, aminoalkyl, thio, thioalkyl, nitro, cyano, alkylcarbonyloxy, alkyloxycarbonyl, alkylcarbonyl, formyl, aminocarbonyl, alkylcarbonylamino, or a moiety of formula (II):

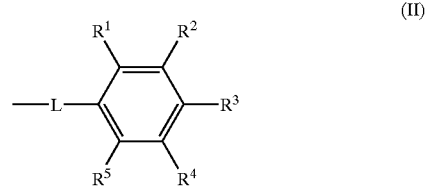
(II)

L is —$L^1$—$L^2$—$L^3$—. $L^2$ is —O—, —S—, —SO—, —$SO_2$—, —N(R')—, —CO—, —N(R')—CO—, —CO—N(R')—, —N(R')—$SO_2$—, —$SO_2$—N(R')—, —O—CO—, —CO—O—, —O—$SO_2$—, —$SO_2$—O—, or deleted. Each of $L^1$ and $L^3$, independently, is —(CR'=CR")$_n$—, —(C≡C)$_n$—, —(C(R')(R"))$_n$—; or deleted. Each of R' and R", independently, is hydrogen, alkyl, alkoxy, hydroxylalkyl, hydroxyl, amino, nitro, cyano, halo, or haloalkyl, and n is 1, 2, or 3. Each of $R^1$, $R^2$, $R^3$, $R^4$, and $R^5$, independently, is hydrogen, alkyl, alkenyl, alkynyl, alkoxy, hydroxyl, hydroxylalkyl, carboxyl, halo, haloalkyl, amino, thio, nitro, cyano, alkylcarbonyloxy, alkyloxycarbonyl, alkylcarbonyl, formyl, aminocarbonyl, alkylcarbonylamino, aminocarbonyloxy, or alkyloxycarbonylamino. Note that when A is an oxygen or a sulfur, both $R^a$ and $R^b$ are deleted; and when A is a nitrogen, $R^a$ is deleted. Further, at least one (e.g., two) of $R^a$, $R^b$, $R^c$, and $R^d$ is a moiety of formula (II) and at least two of $R^1$, $R^2$, $R^3$, $R^4$, and $R^5$ are hydroxyl, alkoxy, or alkylcarbonyloxy which are at meta or ortho positions with respect to each other. A compound of formula (I) also causes a reduction in the levels of some serum nutrients, e.g., glucose, cholesterol, and triglyceride. Accordingly, a method of reducing the level of such serum nutrients using a compound of formula (I) is within the scope of this invention. Note that new compounds of formula (I) and compositions containing one or more of the new compounds, are also within the scope of this invention.

Another aspect of this invention relates to a method for reducing the levels of an endocrine in a subject. The method comprises administering to the subject in need thereof an effective amount of a compound of formula (I), supra. An endocrine is a chemical substance produced in an endocrine system, e.g., a hormone. The endocrines whose levels are affected by a compound of formula (I) include testosterone, estradiol, leptin, insulin, insulin-like growth factor, and luteinizing hormone. A method of inhibiting growth of organs such as prostate, seminal vesicles, coagulating gland, uterus, and ovary by administering a compound of formula (I) is also within the scope of the present invention.

A further aspect of this invention relates to a method of treating a disorder or a disease related to elevated levels of the above-mentioned endocrines or nutrients. The method involves administering to a subject in need thereof an effective amount of a compound of formula (I) decribed above. Some examples of such a disorder or disease are benign prostatic hyperplasia, prostate cancer, skin disorder (e.g., acne), seborrhea, common baldness, hirsutism, hidradenitis suppurative, obesity, breast cancer, ovarian cancer, type II diabetes, cardiovascular diseases, angiogenesis, diabetic retinopathy, rheumatoid arthritis, inflammation, hemagiomas, and psoriasis. The use of a compound of formula (I) for the manufacture of a medicament for treating the above-mentioned disorders or diseases is also within the scope of this invention.

A still further aspect of this invention relates to a liposomal preparation containing a liposome and a compound of formula (I), supra, entrapped therein. The liposome can be formed of lipids such as phosphatidylcholine, phosphatidylethanolamine, phosphotidylserine, cardiolipin, phosphotidylinositol, and cholesterol sulfate.

Set forth below are some examples of compounds of formula (I):

Structure E

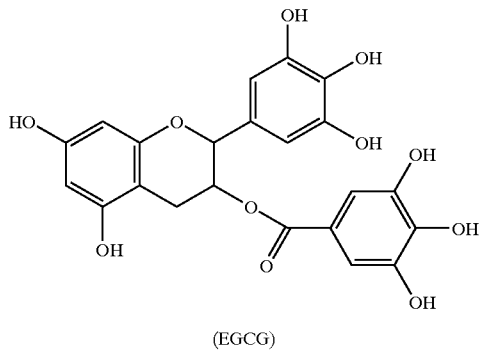

(EGCG)

Structure F

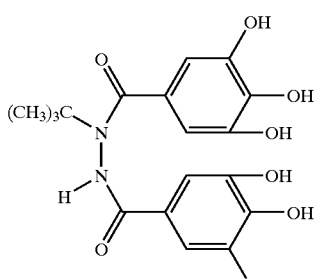

Structure G

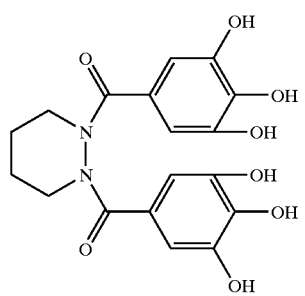

Structure H

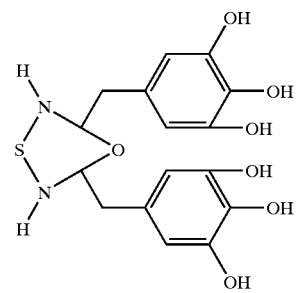

Structure I

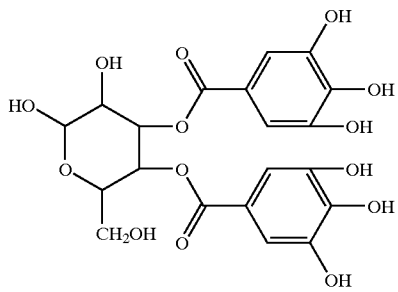

Structure J

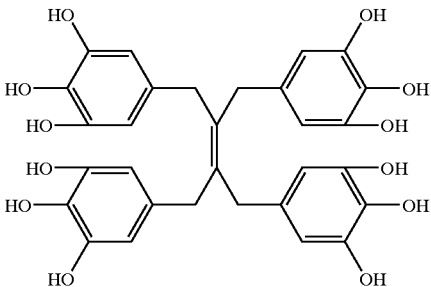

A pharmaceutically acceptable salt of a compound of formula (I) can be formed, for example, between a compound of formula (I) having a carboxylate and a cationic counterion such as an alkali metal cation, e.g., a sodium ion or a potassium ion; or an ammonium cation that can be substituted with organic groups, e.g., a tetramethylammonium ion or a diisopropyl-ethylammonium ion. A salt of a compound of formula (I) can also be formed between a compound of formula (I) having a protonated amino group and an anionic counterion, e.g., a sulfate ion, a nitrate ion, a phosphate ion, or an acetate ion.

It should be recognized that a compound of formula (I) may contain chiral carbon atoms. In other words, it may have optical isomers or diastereoisomers. These isomers are all within the scope of this invention.

As used herein, alkyl is a straight or branched hydrocarbon chain containing 1 to 14 carbon atoms. Examples of alkyl include, but are not limited to, methyl, ethyl, propyl, isopropyl, butyl, isobutyl, sec-butyl, tert-butyl, n-pentyl, 2-methylhexyl, 3-ethyloctyl, and 4-ethyldecyl.

The terms "alkenyl" and "alkynyl" refer to a straight or branched hydrocarbon chain containing 2 to 14 carbon atoms and one or more (e.g., 1–7) double or triple bonds, respectively. Some examples of alkenyl and alkynyl are allyl, 2-butenyl, 2-pentenyl, 2-hexenyl, 2-butynyl, 2-pentynyl and 2-hexynyl.

By cycloalkyl is meant a cyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1–6 heteroatoms such as nitrogen, oxygen, or sulfur. Examples of heterocycloalkyl include piperidinyl, piperazinyl, tetrahydropyranyl, tetrahydrofuryl, and morpholinyl. Cycloalkenyl is a cycloalkyl group containing one or more (e.g., 1–3) double bonds. Examples of such a group include cyclopentenyl, 1,4-cyclohexa-di-enyl, cycloheptenyl, and cyclooctenyl groups. By the same token, heterocycloalkenyl is a heterocycloalkyl group containing one or more double bonds.

As used herein, aryl is an aromatic group containing 6–14 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1–3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

Note that an amino group can be unsubstitued, monosubstituted, or di-substituted. It can be substituted with groups such as alkyl, cycloalkyl, heterocycloalkyl, aryl, heteroaryl, faralkyl, or heteroaralkyl. Halo refers to fluoro, chloro, bromo, or iodo. Some examples of a monosaccharide are pentose and hexose.

Other features or advantages of the present invention will be apparent from the following detailed description, and also from the claims.

DETAILED DESCRIPTION

The invention relates to the use of a polyhydroxylated benzene-containing compound of formula (I), supra, for reducing food intake; lowering the levels of certain endocrines (e.g., testosterone, estradiol, leptin, insulin, insulin-like growth factor-I (IGF-I), and luteinizing hormone (LH)) and nutrients (e.g., glucose, cholesterol, and triglyceride) in the blood; treating or preventing any disorder or disease that is mediated by elevated levels of these endocrines or nutrients; and decreasing the growth of certain organs (e.g., prostate, uterus, and ovary) in a subject. EGCG or its derivatives can be administrated in various methods including intraperitoneal injection or oral administration in the form of a liposomal preparation.

Compounds of formula (I) can be obtained from natural sources. For example, (−)epigallocatechin-3-gallate (EGCG) and (−)epicatechin-3-gallate (ECG) can be isolated from green tea (Camellia sinensis) according to the procedure described in Liao et al., Biochem. Biophys. Res. Commum 214: 833–838 (1995). Some compounds of formula (I), e.g., tannin, are also commercially available from known chemical vendors such as Sigma Chemical Co. (St. Louis, Mo.). Alternatively, Compounds of formula (I) can be prepared synthetically as described below.

Compounds of formula (I), as described above, contains a multiple hydroxylated benzene moiety which is linked to moiety A via a linker L. See formula (II) supra. Compounds of formula (I) wherein L contains an amide bond can be formed by reacting an amine-containing A' with a carboxyl-containing $R^{a'}$. Note that A' and $R^{a'}$ are compounds which, upon reacting with each other, yield moieties of A and $R^a$, respectively. Referring to the first reaction shown scheme I below, compound A' is gallic acid and compound $R^{a'}$ is 6-hydroxydopamine. These two compounds are coupled in the presence of a common coupling reagent such as 1-ethyl-3-(3-dimethylaminopropyl)carbodiimide (EDC), benzotriazol-1-yloxytris(dimethylamino)-phosphonium hexafluorophosphate (BOP), or O-benzo-triazol-1-yl-N,N,N',N'-tetramethyluronium hexafluorophosphate (HBTU) to form compound X. Similarly, caffeic acid and 3-O-methydopamine can be coupled to form compound XII. See the last reaction of Scheme I. Compound XI, wherein L contains a carbonyl, can be prepared by reacting methyl 3,4,5-trimethoxybenzoate with 4-dimethylaminiobenzaldehyde in an alkaline medium. See the second reaction of Scheme I.

Scheme I

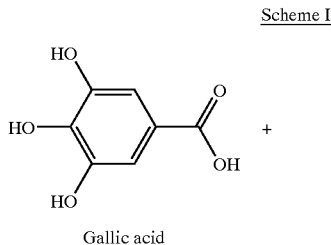

Gallic acid

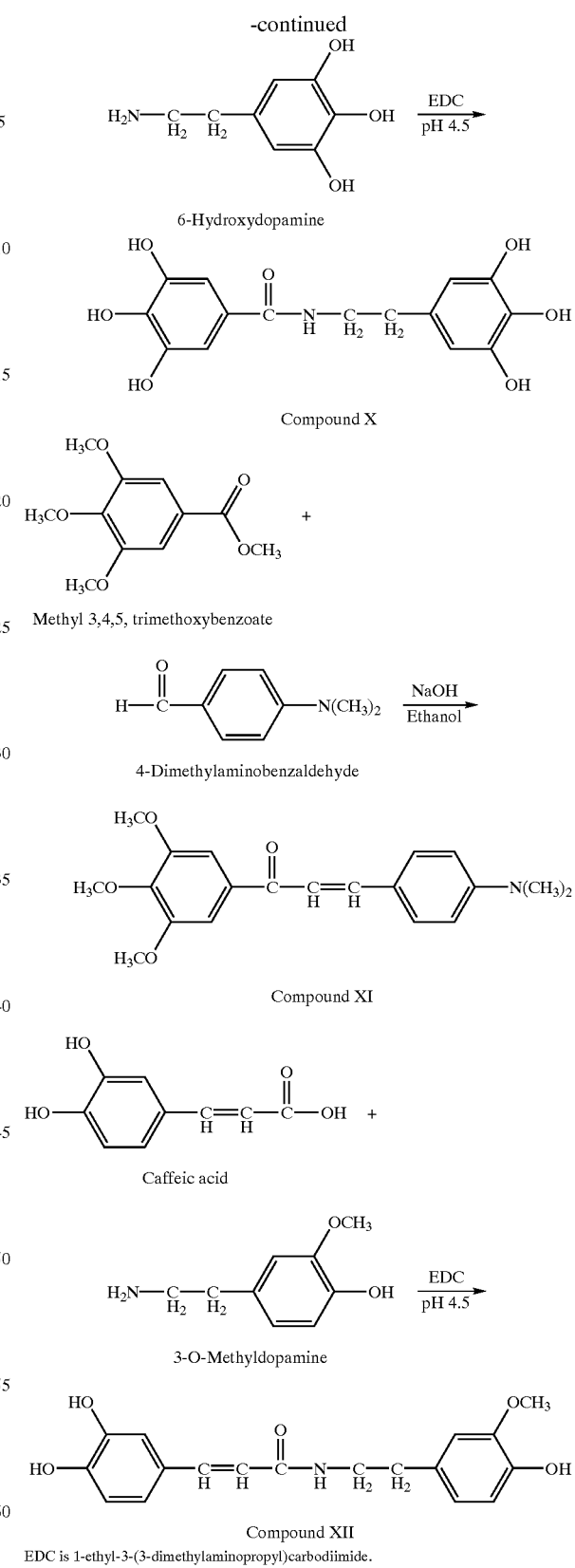

Schemes II–V below describe methods of preparing compounds of formula (I) in which A is an alkenyl or an aryl.

Scheme II

Following schem shows how complex gallate derivative, such as compound K can be synthesized. The oxidative coupling on the enolate of 3′,4′,5′-trimethoxyacetophenone (1) gave the 1,4-dione (2). Compound 2 was converted to 3 by bromination followed by dehydro-bromination reaction. Demethylation of 3 with BBr3 furnished trans-K, which was transformed to cis-K by the irradiation of light in the acetone solution.

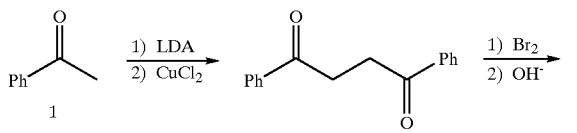

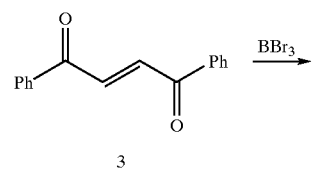

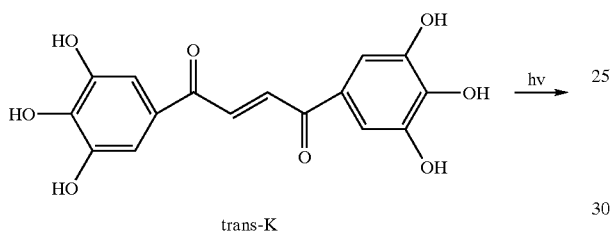

trans-K

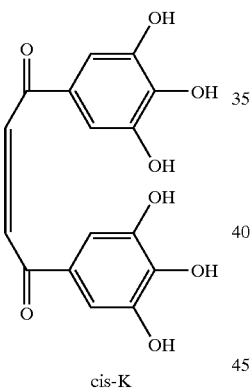

cis-K

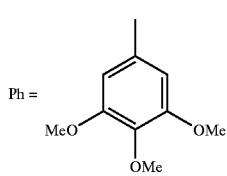

Ph =

Scheme III

Compounds with four hydroxyl benzenes, like Compound J can be synthesized as depicted in the following scheme. 3′,4′,5′-Trimethoxybenzyl alcohol (1) was converted to 3′,4′,5′-trimethoxyphenylacetate (5) in four steps. Compound 5 was treated with LDA and then hydrolyzed to give 1,3-bis(3′,4′,5′-trimethoxyphenyl)acetone (6). The reductive coupling of 6 with low-valent titanium afforded the corresponding tetrabenzylethylene (7), which was demethylated with BBr3 to gave compound (structure J) .

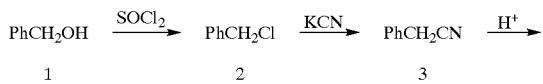

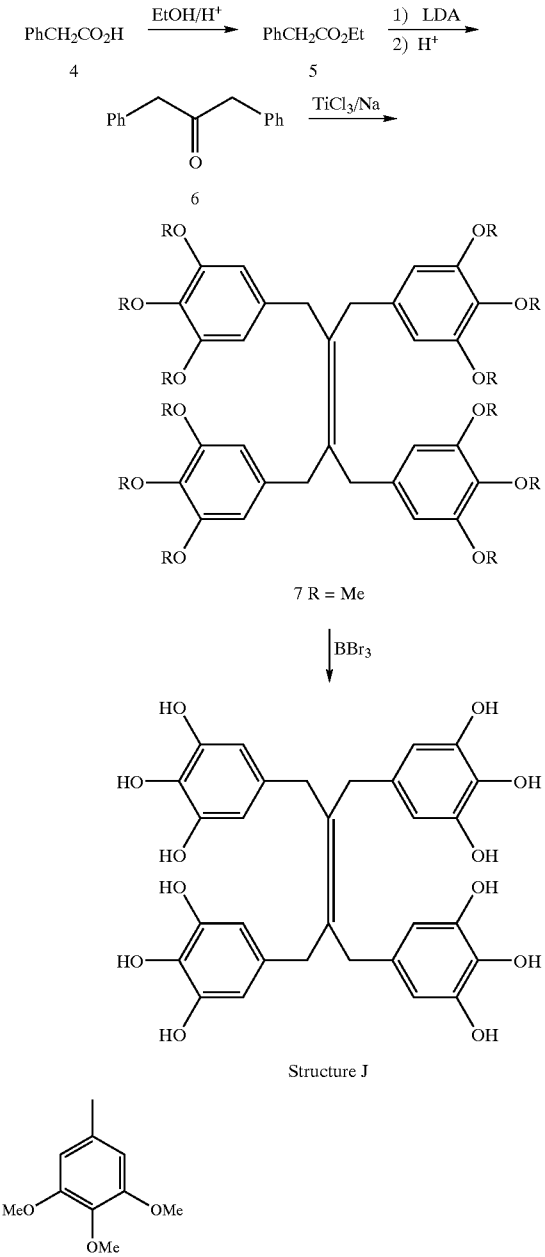

Structure J

Ph =

Scheme IV

The condensation reaction of 3′,4′,5′-trimethoxyacetophenone (1) and ethyl 3′,4′,5′-trimethoxybenzoate (2) gave 1,3-bis(3′,4′,5′-trimethoxyphenyl)-1,3-propanedione (3). The addition of 4-phenyltriazolinedione to 3 afforded the 2-urazolyl-1,3-propanedione, which was oxidized to the corresponding N-phenyltriazolinedione ylide (4) with tert-butyl hypochlorite (t-BuOCl). The ylid (4) was treated with the enolate of 3 to afford the corresponding tetrabenzoylethylene (5), whi ch was demethylated to give Compound J2.

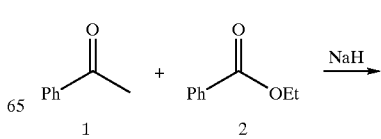

Scheme V

Acetylation of EGC, followed by selective deacetylation in Tris buffer pH 8.2 gives the monacetate 2. Silylation of the phenolic hydroxyl groups and subsequent deacetylation afforded pentasilylated epigallocatechin 4. Myristoleic acid (MOA) ester of 4 was prepared by transesterification with MOA in the presence of DCC (dicyclohexylcarbodiimide) and DMAP 9-dimethylaminopyridine). Deprotection of 5 with triethylamine trihydroflouride provided EGC-MOA 6 in satisfactory yields.

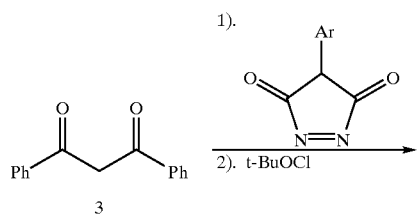

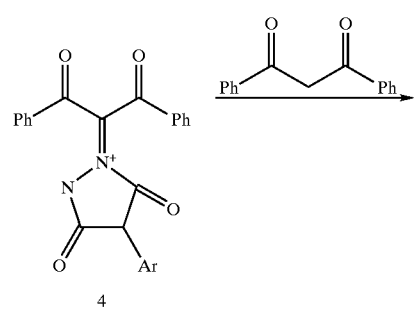

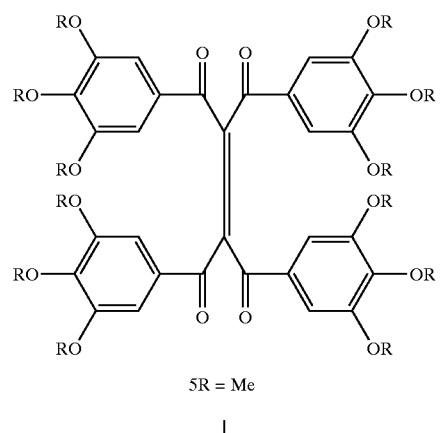

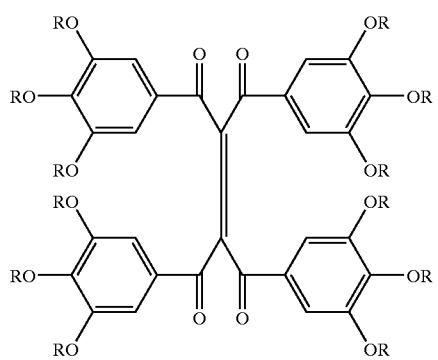

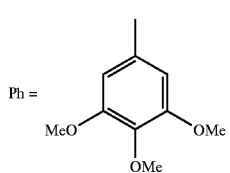

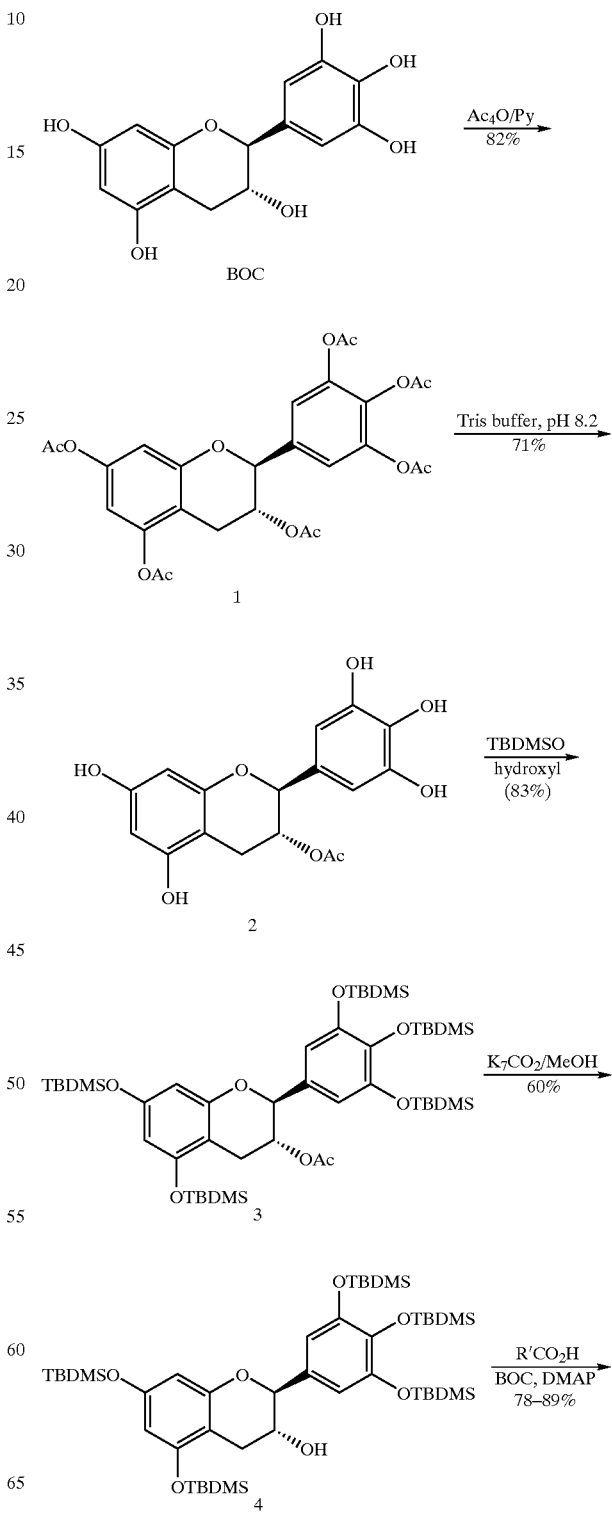

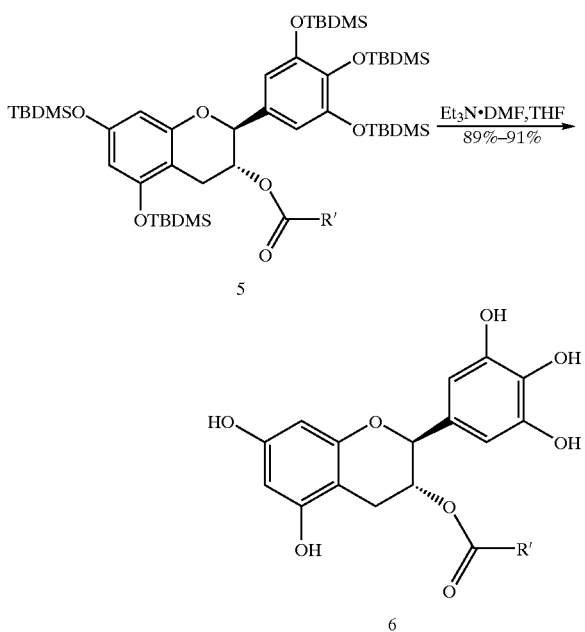

Compounds of formula (I) prepared by synthetic methods discussed above can be purified by flash column chromatography, preparative high performance liquid chromatography, or crystallization.

As mentioned above, a compound of formula (I), reduces food intake and inhibits growth of organs such as prostate, seminal vesicles, coagulating gland, uterus, and ovary. It also reduces the circulating levels of certain endocrines and nutrients in the subject. Such endocrines and nutrients include testosterone, estradiol, leptin, insulin, insulin-like growth factor-I, luteinizing hormone, glucose, cholesterol, and triglyceride. Diseases or conditions relating to elevated levels of the just-mentioned endocrines and nutrients include benign prostatic hyperplasia, prostate cancer, skin disorder (e.g., acne), seborrhea, common baldness, hirsutism, hidradenitis suppurative, obesity, breast cancer, ovarian cancer, type II diabetes, cardiovascular diseases, angiogenesis, diabetic retinopathy, rheumatoid arthritis, inflammation, hemagiomas, and psoriasis. All of the just-mentioned conditions or diseases are treatable by administering an effective amount of a compound of formula (I) or its salt to a subject in need thereof.

An effective amount is defined as the amount of a compound of formula (I) which, upon administration to a subject in need, confers a therapeutic effect on the treated subject. The effective amount to be administered to a subject is typically based on body surface area, subject weight, and subject condition. The interrelationship of dosages for subjects (based on milligrams per meter squared of body surface) is described by Freireich et al., Cancer Chemother. Rep. 1966, 50, 219. Body surface area may be approximately determined from height and weight of the subject. See, e.g., Scientific Tables, Geigy Pharmaceuticals, Ardley, N.Y., 1970, 537. An effective amount of a compound of formula (I) used to practice the invention can range from about 1 mg/kg to about 2 g/kg, e.g., from about 1 mg/kg to about 1 g/kg, from about 1 mg/kg to about 500 mg/kg, or from about 1 mg/kg to about 150 mg/kg. Effective doses will also vary, as recognized by those skilled in the art, dependant on route of administration, excipient usage, and the possibility of co-usage with other therapeutic treatments.

A pharmaceutical composition containing a compound of formula (I) may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

Compounds of formula (I) can also be formulated into dosage forms for other routes of administration utilizing well-known methods. They can be formulated, for example, in dosage forms for oral administration in a gel seal, a syrup, a capsule, or a tablet. Capsules may comprise any well-known pharmaceutically acceptable material such as gelatin or cellulose derivatives. Tablets may be formulated in accordance with the conventional procedure by compressing mixtures of the compound of this invention and a solid carrier, and a lubricant. Examples of solid carriers include starch and sugar bentonite. The steroid derivatives of this invention can also be administered in a form of a hard shell tablet or a capsule containing a binder (e.g., lactose or mannitol) and a conventional filler.

Compounds of formula (I) can be administered via any appropriate route, e.g. intravenously, intraarterialiy, topically, by injection, intraperitoneally, intrapleurally, orally, subcutaneously, intramuscularly, sublingually, intraepidermally, or rectally. It can be formulated as a solution, suspension, suppository, tablet, granules, powder, capsules, ointment, or cream. In the preparation of these compositions, a solvent (e.g., water or physiological saline), solubilizing agent (e.g., ethanol, Polysorbates, or Cremophor EL7), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane can be added. Pharmaceutical preparations such as solutions, tablets, granules or capsules can be formed with these components.

A method for orally administering a compound of formula (I) is by administering a liposomal preparation containing a liposome and a compound of formula (I) entrapped therein. Liposomes are lipid bilayer vesicles that form spontaneously, in the presence of water. Liposomes can be made from a variety of amphiphilic lipids. Phosphatidylcholine is the most common phospholipid used to make liposomes, but other amphiphilic lipids, such as phosphatidylethanolamine, phosphotidylserine, cardilipin, phosphotidylinositol, and cholesterol sulfate can also be used. Liposomes can be made using a single type of lipid or can be composed of a mixture of components. For example cholesterol (or other sterols) is often added to liposomes composed of phosphatidylcholine to stabilize them in biological fluids. Depending on the preparative method employed, multilammelar and/or unilamellar vesicles are formed. These vesicles can be either large (0.1–100 µm) or small (0.025–0.1 µm) in diameter. Multilamellar liposomes, which are the type being used in this project, are made by dissolving lipids and nonpolar drugs in organic solvent and then the mixture is dried on the walls of a glass vesicle under reduced pressure. An aqueous buffer containing a compound of formula (I), e.g., EGCG, is then added and the mixture shaken vigorously to disperse the lipids. This step must be performed above the gel-liquid-crystalline phase transition temperature for a gene lipid composition. This temperature depends on the individual components of the liposomes and on, the fatty acid composition of the phospholipids in the liposome. Alternatively, liposomes loaded with a desired compound can be made by dissolving phopholipids and compound in a solvent such as acetone, and then isolating a complex of the two by precipitating them in a solvent, such as hexane or lyophilizing or spray drying the components. When this material is suspended in aqueous solvents, a liposomal complex is spontaneously formed. A dried liposomal preparation of a compound of formula (I) is stable, especially when stored under vacuum and low temperatures. Addition of antioxidants, such as ascorbic acid or butylated hydroxytoluene (BHT), may allow storage of the preparation at room temperature and ambient pressures.

Without further elaboration, it is believed that one skilled in the art can, based on the above disclosure and the description below, utilize the present invention to its fullest extent. The following examples, which describe syntheses, biological activities and formulation of a compound of formula (I), are to be construed as merely illustrative of how one skilled in the art can practice the invention and are not limitative of the remainder of the disclosure in any way. Any publications cited in this disclosure are hereby incorporated by reference.

EXAMPLES

Compounds of formula (I) were prepared according to methods described below:

Preparation of N-t-butyl-N,N'-di-2,3,4-trihydroxybenzoyl-hydrazine. 2,3,4-trihydoxybenzoic acid (10 mmol) was refluxed with thionyl chloride (20 mol) for 3 hours. After evaporating the excess thionyl chloride under reduced pressure, 2,3,4-trihydroxybenzoyl chloride was purified by distillation. 2,3,4-trihydroxybenzoyl chloride (10 mmol) and a 50% aqueous solution of sodium hydroxide (20 mmol) was simultaneously added dropwise to a suspension of t-butylhydrazine hydrochloride (10 mmol) in 100 ml of 1,4-dioxane/water (2:1,v/v) with stirring on an ice bath. After stirring for 2 days at room temperature, dioxane was removed under reduced pressure and the residue was extracted with ether. The organic phase was washed once with 1 N NaOH and brine and then dried over anhydrous magnesium sulfate. The residue obtained by evaporation of the ether under reduced pressure was purified by silica-gel column chromatography with hexane/ethyl acetate (1:1, v/v) to afford N-t-butyl-N,N'-di-2,3,4-trihydroxybenzoyl-hydrazine.

Preparation of N,N'-di-ethyl-N,N'-di-2,3,4-trihydroxybenzoyl-hyrazine. The same procedure as described above was employed except that t-butylhydrazine hydrochloride was replaced with diethylhydrazine dihydrochloride.

The activities of a compound of formula (I), (−)epigallocatechin-3-gallate (EGCG), were discovered using the following materials and methods:

Animal. Adult Sprague-Dawley (SD; Harlan) rats (body weight for male: 170–190 g; for female: 125–145 g) and lean and obese Zucker (Charles River Laboratory) rats (body weight for lean male: 240–260 g; for obese male: 420–440 g) were given free access to a standard rat chow diet and water unless indicated. Animal experimental protocols were approved by the University of Chicago institutional animal care and use committee. Rats were maintained at an ambient temperature of 25° C. under a photoperiod of 12-hour light and 12-hour dark.

In vivo treatment. EGCG and other catechins (>98% pure) were isolated from green tea (*Camellia sinensis*) in our laboratory as described in Liao et al., Biochem. Biophys. Res. Commun. 214: 833–838 (1995). Catechins were dissolved in water for oral administration and in sterile phosphate buffered saline for ip injection. Rats in control groups received vehicle only. Testosterone propionate (TP) and 5α-dihydrotestosterone propionate (DHTP) were dissolved in sesame oil and 4 mg in 0.5 ml sesame oil (16 mg/kg body weight) was injected subcutaneously daily, when indicated.

Food-restricted, male SD rats were given 12 g rat chow daily, which was about 50% of the amount consumed daily by each control rat. The body weight and the amount of food and water consumed were monitored daily. Food consumption was monitored in rats caged in groups of 3 to 5 animals by weighing food pellets every 24 hr. On the final day, rats were anesthetized with methoxyflurane and blood was collected by heart puncture. Sera were collected after centrifugation (10,000 g for 20 min at 4° C.) for biochemical analysis.

Biochemical analysis. For biochemical analysis, commercially available radioimmunoassay kits for IGF-I and testosterone (Diagnostic Systems Laboratory, Inc), LH and GH (Amersham), leptin and insulin (Linco Research Inc), and corticosterone (ICN) and analytical kits for glycerol and triglyceride (Sigma) and fatty acids (Roche Molecular Biochemicals) were used. Proximate composition analysis of rats was performed by COVANCE Laboratory (Madison, Wis.). Complete blood count and serum chemistry (e.g., cholesterols, glucose, and enzymatic activities) were performed by the Animal Resource Center at the University of Chicago.

Statistical analysis. Data are expressed as the mean±sem. The unpaired Student's t-test was used to examine differences between control and the EGCG-injected groups. Analysis of variance and Student-Newman-Keuls multiple range test were used to examine differences among various groups. A probability level of 0.05 was used to indicate significance.

Body weight of subjects treated with EGCG. IP injection of EGCG caused acute body weight loss in SD male and female rats within 2 to 7 days of treatment. In male SD rats, the effect of EGCG on body weight was dose-dependent. Doses of 5 or 10 mg of EGCG (26 and 53 mg/kg body weight) injected daily were not effective or less effective in reducing the body weight than 15 mg (about 85 mg/kg body weight). Male SD rats injected daily ip with 26 and 53 mg EGCG/kg bw gained body weight by 17–24% relative to their initial body weight, but lost 5–9% relative to the control after 7 days of treatment. Whereas, male SD rats daily injected ip with 85 mg EGCG/kg bw lost 15–21% of their body weight relative to their initial weight and 30–41% relative to the control after 7 days of treatment. Control rats continued growth and increased their body weight by 25–34% relative to their initial weight (see Table 1). Female SD rats injected daily ip with 12.5 mg EGCG (about 92 mg/kg bw) lost 10% of their body weight relative to their initial weight and 29% relative to the control after 7 days of treatment. Therefore, a dose of EGCG of 70–92 mg/kg body weight was used in most experiments.

Weight change in accessory sexual organs and other organs. An effect of EGCG dosage on the weight of accessory sexual organs was also observed. The weight of androgen-sensitive organs, such as ventral and dorsolateral prostates, seminal vesicles, coagulating glands, and preputial glands were reduced by 50–70% after 7 days of treatment with EGCG (about 85 mg/kg bw). Weight changes in these sexual organs were modulated in a catechin-specific manner. Relative to control animals sacrificed at the start of the experiment, these accessory sexual organs (except preputial gland) in male SD rats were reduced by 30–50% in weight after 7 days of EGCG treatment. Similarly, the weight of estrogen-sensitive organs, e.g., uterus and ovary, of female SD rats was reduced by about 50% after 7 days of BGCG treatment. The weight of each of liver and kidney was also decreased by about 20%. In male SD and lean Zucker rats treated with EGCG for 7–8 days, the weight of each of liver, kidney and testis was reduced by about 10–20%, while the spleen weight was reduced by about 15–30%. However, there was no change in weight of the just-mentioned organs in male obese Zucker rats treated with EGCG for 4 days.

Change in levels of sex hormones, leptin, IGF-I, insulin, LH and GH. Rats treated with EGCG had significant changes in various endocrine parameters. After 7 days of treatment with EGCG (about 85 mg/kg bw), circulating testosterone was reduced by about 70% in male SD rats. Similarly, the circulating level of 17β-estradiol was reduced by 34% in females after 7 days of EGCG treatment. In both male and female SD rats, 7 days of EGCG treatment caused significant reduction in blood levels of leptin, IGF-I, and insulin. Dose-dependent effects of EGCG in male SD rats were also observed on levels of serum testosterone, leptin, IGF-I and insulin. As to male and female SD rats treated with EGCG for 7 days, the serum level of LH was also significantly reduced (40–50%) while that of GH was increased in males or reduced in females. However, the pulsatile nature of GH secretion prevented us from making definite conclusions about changes in circulating levels of GH in these rats. The effect of EGCG on sex hormones and various peptide hormones investigated was not mimicked by ECG which has one less hydroxyl group than EGCG.

Lean and obese male Zucker rats treated with EGCG also showed similar changes in the serum levels of testosterone, leptin, IGF-I, insulin and GH and prostate weight. For both SD and Zucker rats, significant effects were observed with 70–92 mg EGCG per kg of body weight.

Effects of exogenous androgen reverses the effect of EGCG on accessory sexual organs. To determine if the reduction in weight of accessory sexual organs was due to EGCG-induced reduction in androgen levels, we injected male SD rats with androgen and/or EGCG. We found that EGCG did not cause prostate weight loss in male rats injected daily with TP or DHTP; therefore, the EGCG effect on prostate weight was most likely secondary to the EGCG-induced reduction in the level of testosterone in these male rats. However, androgen administration was not able to prevent the EGCG-induced body weight loss, food intake restriction, decreases in the circulating leptin, IGF-I, insulin, and LH, and increase in circulating GH.

Change in serum nutrients and proximate body composition. In EGCG-treated male SD rats, the serum level of protein, fatty acids and glycerol were not altered, but significant reductions in serum glucose (−32%), lipids (−15%), triglycerides (−46%) and cholesterol (−20%) were observed. Similar changes in these serum nutrients were observed in male lean and obese Zucker rats. Proximate composition analysis of animals showed that SD rats treated daily with EGCG for 7 days had no change in percent water and protein content, a moderate decrease in carbohydrate content (2.5% in control and 1.3% in EGCG-treated group), but a very large reduction in fat content (from 4.1% in control to 1.4% in EGCG-treated group). Within 7 to 8 days, EGCG treatment decreased subcutaneous fat by 40–70% and abdominal fat by 20–35%, but not epididymal fat, in male SD and lean Zucker rats. A 20% loss of abdominal fat was seen in obese male Zucker rats within 4 days of EGCG treatment.

Effect of EGCG on Food intake. We found that EGCG-treated SD male and female rats consumed about 50–60% less food than control rats. Similar effects of EGCG on food intake were observed with obese male Zucker rats. Therefore, body weight loss was due to reduced intake of food. Since food restriction can alter hypothalamic function and decrease the level of LH and sex steroids, we restricted the food intake of SD male rats (not injected with EGCG) by about 50% for 7 days and found that the blood level of testosterone was indeed reduced by about 60% and ventral prostate weight was decreased by about 50% compared to animals given free access to food. Serum leptin, IGF-I, insulin, LH, and GH were also decreased after food restriction. Administration of androgen to male SD, rats was not able to prevent the EGCG-induced food intake reduction. These effects of EGCG, administered intraperitoneally, were diminished or absent when EGCG was administered orally.

Change in composition of blood. Male SD rats were treated with EGCG and ECG for 7 days and then their serum and whole blood was analyzed for various components. Neither EGCG nor structurally-related ECG caused significant changes in the serum level of total protein, albumin, blood urea nitrogen, creatine, $PO_4^{3-}$, $Na^+$, $K^+$, $Ca^{2+}$, $Cl^-$, and enzymes that are indicative of severe damage to liver and other organs, such as lactate dehydrogenase, alanine aminotransferase, aspartate aminotransferase, and γ-glutamyltranspeptidase. However, significant changes in the amount of blood bilirubin and the activity of blood alkaline phosphatase were observed. In blood of rats treated with EGCG, red blood cell and hemoglobin concentrations increased by about 20%, whereas the concentration of white blood cells, lymphocytes, and monocytes decreased about 10%, 31%, and 24% respectively. Both eosinophil and platelet concentrations increased by 100%.

The following example describes a procedure for forming and testing a liposomal preparation containing EGCG:

Preparation of a EGCG-soy phosphatidylcholine (PC) complex (SPC). A suspension of 7.6 g of PC and 4.58 g of EGCG is made in 150 ml of acetone. After mixing for 3 hours at room temperature the solution is concentrated under vacuum to 30 ml and then diluted slowly with 300 ml of hexane. The precipitate that forms after standing for 18 h is collected by filtration, dried under vacuum and stored under vacuum in the dark at −20° C.

Determination of bioavailability of EGCG-SPC using cells in culture. The EGCG-SPC complex is suspended in PBS at a concentration of 12 mg/ml (equivalent to 10 mM EGCG). HEK293 cells expressing either the type 1 or 2 human 5α-reductase are seeded on 24 well plates at concentration of 50,000 cells/well. The next day various doses of EGCG-SPC are added such that the concentration of EGCG would be equivalent to 0–100 µM. A control liposomal preparation will consist of SPC made without EGCG and will be tested at concentrations of PC equivalent to that used for EGCG-SPC. After a 1 hour incubation, [$^{14}$C]-testosterone (55 mCi/mmol) is added (final concentration 1 µM) and the cells incubated at 37° C. for 1 hour. Media is then removed and extracted with ethylacetate After concentration, the extract is separated by TLC using silica gel plates and the solvent methylene chloride/ethylacetate/ methanol (85:15:3). The plate is then scanned for radioactivity using a Molecular Dynamics Storm phosphoimager/ scanner. The relative amounts of radioactivity in spots corresponding to T and DHT is then determined. The concentration of EGCG-SPC inhibiting 5α-reductase activity by 50% (IC$_{50}$) is determined graphically.

Administration of EGCG-SPC to rats. The ECGC-SPC is suspended in PBS at a concentration of 120 mg/ml and 2 ml (equivalent to 92 mg EGCG) is administered by gavage to each rat in a group of 35 (190–200 g) male Sprague Dawley rats. Another group of rats will receive an equivalent dose (92 mg) of pure EGCG in PBS for comparison. At 0, 0.5, 1, 2, 3, 4 and 5 h, five rats are bleed out by cardiac puncture, while anesthetized with metofane. Blood is collected into heparinized tubes and after centrifugation the plasma is mixed with 0.1 volumes of 20% ascorbic acid and –0.05% EDTA. This lowers the pH and chelates iron, which stabilizes EGCG. The protocol will be repeated using different doses of EGCG-SPC to determine if there is a linear dose-response relationship between the dose administered and blood levels of EGCG.

Analysis of plasma EGCG in rats. Plasma is thawed on ice and 1 ml aliquots are mixed with 0.1 volume PBS or 0.1 volume of PBS containing β-glucuronidase (2500 U) and sulfatase (200 U). Samples are incubated for 1 h at 37° C. and then extracted twice with equal volumes of ethylacetate. The ethylacetate is removed under vacuum and then extracted twice with equal volumes of ethylacetate. The ethylacetate is removed under vacuum and then the dried extract dissolved in 100 µl of HPLC solvent consisting of acetonitrile/ethylacetate/0.05% phosphoric acid (12:2:86). The sample is separated on an analytical C18 column using isocratic elution at 40° C. with UV detection at 273 nm. Pure EGCG is used to prepare standard solutions to quantitative EGCG in plasma by comparing peak heights of standards and unknowns. Since EGCG can breakdown into EGC and gallate by nonenzymatic and through the action of nonspecific esterase in blood, both EGCG and EGC peak will be monitored by HPLC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method for reducing food intake in a subject, the method comprising administering to the subject in need thereof an effective amount of a compound of the formula:

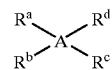

wherein

A is alkenyl; and each of $R^a$, $R^b$, $R^c$ and $R^d$ is a moiety of the formula:

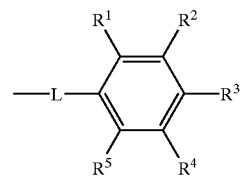

in which L is —L$^1$—L$^2$—L$^3$— wherein L$^2$ is deleted, L$^1$ is —(C(R')(R"))$_n$—, and L$^3$ is deleted; each of R' and R" is hydrogen and n is 1; each of R$^1$ and R$^5$ is hydrogen, and each of R$^2$, R$^3$, and R$^4$ is hydroxyl; or a pharmaceutically acceptable salt thereof.

2. A method for reducing the levels of an endocrine in a subject, the method comprising administering to the subject in need thereof an effective amount of a compound of the formula:

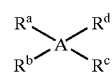

wherein

A is alkenyl; and each of $R^a$, $R^b$, $R^c$ and $R^d$ is a moiety of the formula:

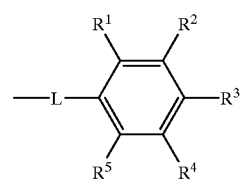

in which L is —L$^1$—L$^2$—L$^3$— wherein L$^2$ is deleted, L$^1$ is —(C(R')(R"))$_n$—, and L$^3$ is deleted; each of R' and R" is hydrogen, and n is 1; each of R$^1$ and R$^5$ is hydrogen, and each of R$^2$, R$^3$, and R$^4$ is hydroxyl; or a pharmaceutically acceptable salt thereof;

said endocrine being selected from the group consisting of testosterone, estradiol, leptin, insulin, insulin-like growth factor, and luteinizing hormone.

* * * * *